United States Patent [19]

Bundy

[11] 4,267,315
[45] May 12, 1981

[54] 2-DECARBOXY-2-AMINOMETHYL-11A-METHANO-TXA$_2$ COMPOUNDS

[75] Inventor: Gordon L. Bundy, Portage, Mich.

[73] Assignee: The Upjohn Company, Kalamazoo, Mich.

[21] Appl. No.: 116,079

[22] Filed: Jan. 28, 1980

Related U.S. Application Data

[62] Division of Ser. No. 35,143, May 1, 1979, Pat. No. 4,218,378.

[51] Int. Cl.$^3$ .................. C09B 23/00; C09B 23/16; C07D 301/00
[52] U.S. Cl. .................................. 542/400; 542/413; 260/333
[58] Field of Search .................. 260/563 R, 570.8 R, 260/570.5 CA, 333; 542/400, 413

[56] References Cited

U.S. PATENT DOCUMENTS

| | | | |
|---|---|---|---|
| 3,993,674 | 11/1976 | Schaub | 260/410.9 P |
| 4,073,808 | 2/1978 | Nelson | 260/563 R |
| 4,107,427 | 8/1978 | Kelly | 560/177 |

OTHER PUBLICATIONS

Samuelsson, B. et al., *Advances in Prostaglandin and Thromboxane Research*, (New York), p. 5.

*Primary Examiner*—John F. Niebling
*Attorney, Agent, or Firm*—Robert A. Armitage

[57] ABSTRACT

The present invention provides novel thromboxane analogs and intermediates. Particularly, the present invention provides novel 2-decarboxy-2-aminomethyl-11a-methano-TXA$_2$ compounds.

3 Claims, No Drawings

2-DECARBOXY-2-AMINOMETHYL-11A-METHANO-TXA$_2$ COMPOUNDS

DESCRIPTION

CROSS REFERENCE TO RELATED APPLICATION

The present application is a division of Ser. No. 035,143, filed May 1, 1979, now U.S. Pat. No. 4,218,378.

BACKGROUND OF THE INVENTION

The present invention provides novel thromboxane analogs and intermediates. Particularly, the present invention provides novel 2-decarboxy-2-aminomethyl-11a-methano-TXA$_2$ compounds. The essential material constituting a disclosure of the preparation and use of the compounds described above is incorporated here by reference from the U. S. Ser. No. 035,143, now U.S. Pat. No. 4,218,378.

PRIOR ART

As indicated above, thromboxane A$_2$ is known in the art. See Hamberg, M., et al., Proceedings of the National Academy of Sciences U.S.A. 72:2994 (1975), Samuelsson, Proceedings of the National Academy of Sciences U.S.A. 71:3400-3404 (1974). Likewise, numerous analogs of thromboxane B$_2$ and their use as reproductive cycle control agents is known in the art. See U.S. Pat. No. 4,070,384, issued Jan. 24, 1978.

Other heterocyclic ring analogs of the prostaglandins include the 9α,11α- or 11α,9α-epoxymethano-9,11-dideoxy-PGF-type compounds described in U.S. Pat. Nos. 3,950,363 and 4,028,354. Finally related azo and epoxyimino compounds are known in the art. See U.S. Pat. No. 4,112,224.

SUMMARY OF THE INVENTION

The present invention particularly provides a thromboxane analog of formula XI

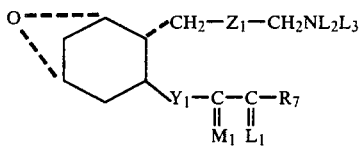

wherein Y$_1$ is
(1) trans—CH=CH—,
(2) cis—CH=CH—,
(3) —CH$_2$CH$_2$—, or
(4) —C≡C—, wherein M$_1$ is α-R$_5$:β-OH, α-OH:β-R$_5$, or α-H:β-H, wherein R$_5$ is hydrogen or methyl, and wherein L$_1$ is α-R$_3$:β-R$_4$, α-R$_4$:β-R$_3$, or a mixture of α-R$_3$:β-R$_4$ and β-R$_3$:α-R$_4$, wherein R$_3$ and R$_4$ are hydrogen, methyl, or fluoro, being the same or different, with the proviso that one of R$_3$ and R$_4$ is fluoro only when the other is hydrogen or fluoro, or wherein —C(M$_1$)—C(L$_1$)— is trans—CH=CH—;

wherein Z$_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —(CH$_2$)$_2$—O—(CH$_2$)$_g$—CH$_2$—, or
(8) trans—CH$_2$—(CH$_2$)$_g$—CH$_2$—CH=CH—;
(9) —(m-Ph)—O—(CH$_2$)$_g$—, or
(10) —(m-Ph)—CH$_2$—(CH$_2$)$_g$—,
wherein g is one, 2, or 3 and —(m-Ph)— is meta-phenylene;

wherein R$_7$ is
(1) —(CH$_2$)$_m$—CH$_3$, wherein m is an integer from one to 5, inclusive;
(2) phenoxy;
(3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that R$_7$ is phenoxy or substituted phenoxy, only when R$_3$ and R$_4$ are hydrogen or methyl, being the same or different; and wherein L$_2$ and L$_3$ are hydrogen or alkyl of one to 4 carbon atoms, inclusive, being the same or different, or a pharmacologically acceptable acid addition salt thereof.

DESCRIPTION OF PREFERRED EMBODIMENTS

The specific embodiments of the present invention include:
2-decarboxy-2-aminomethyl-11a-methano-TXA$_2$
2-decarboxy-2-aminomethyl-11a-methano-15-deoxy-TXA$_2$ The novel 11a-methano-TXA analogs of the present invention are as 11 highly active as inhibitors of thromboxane synthetase and accordingly are useful for anti-inflammatory, anti-asthma and anti-thrombotic indications.

I claim:
1. A thromboxane analog of formula IV

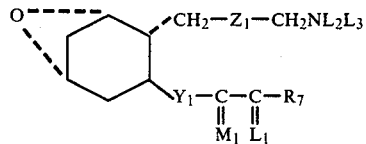

wherein Y$_1$ is
(1) trans—CH=CH—,
(2) cis—CH=CH—,
(3) —CH$_2$CH$_2$—, or
(4) —C≡C—, wherein M$_1$ is α-R$_5$:β-OH, α-OH:β-R$_5$, or α-H:β-H, wherein R$_5$ is hydrogen or methyl, and wherein L$_1$ is α-R$_3$:β-R$_4$, α-R$_4$:β-R$_3$, or a mixture of α-R$_3$:β-R$_4$ and β-R$_3$:α-R$_4$, wherein R$_3$ and R$_4$ are hydrogen, methyl, or fluoro, being the same or different, with the proviso that one of $R_3$ and $R_4$ is fluoro only when the other is hydrogen or fluoro, or wherein $-C(M_1)-C(L_1)-$ is trans-$CH=CH-$;

wherein $Z_1$ is
(1) cis-$CH=CH-CH_2-(CH_2)_g-CH_2-$,
(2) cis-$CH=CH-CH_2-(CH_2)_g-CF_2-$,
(3) cis-$CH_2-CH=CH-(CH_2)_g-CH_2-$,
(4) $-(CH_2)_3-(CH_2)_g-CH_2-$,
(5) $-(CH_2)_3-(CH_2)_g-CF_2-$,
(6) $-CH_2-O-CH_2-(CH_2)_g-CH_2-$,
(7) $-(CH_2)_2-O-(CH_2)_g-CH_2-$,
(8) trans-$CH_2-(CH_2)_g-CH_2-CH=CH-$,
(9) $-(m-Ph)-O-(CH_2)_g-$, or
(10) $-(m-Ph)-CH_2-(CH_2)_g-$,
wherein g is one, 2, or 3, and $-(m-Ph)-$ is meta-phenylene;

wherein $R_7$ is
(1) $-(CH_2)_m-CH_3$, wherein m is an integer from one to 5, inclusive;
(2) phenoxy;
(3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl of one to 3 carbon atoms inclusive, or alkoxy of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different; and wherein $L_2$ and $L_3$ are hydrogen or alkyl of one to 4 carbon atoms, inclusive, being the same or different, or a pharmacologically acceptable acid addition salt thereof.

2. 2-Decarboxy-2-aminomethyl-11a-methano-$TXA_2$, a compound according to claim 1.

3. 2-Decarboxy-2-aminomethyl-11a-methano-15-deoxy-$TXA_2$, a compound according to claim 1.

* * * * *